(12) United States Patent
Woerner et al.

(10) Patent No.: US 10,632,097 B2
(45) Date of Patent: Apr. 28, 2020

(54) ORGANOMETALLIC COMPOUND

(71) Applicant: Umicore AG & Co. KG, Hanau-Wolfgang (DE)

(72) Inventors: Eileen Woerner, Nidderau (DE); Ralf Karch, Kleinostheim (DE); Andreas Rivas-Nass, Bensheim (DE); Angelino Doppiu, Seligenstadt (DE); Annika Frey, Hanau (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 0 days.

(21) Appl. No.: 15/555,800

(22) PCT Filed: Feb. 29, 2016

(86) PCT No.: PCT/EP2016/054234
§ 371 (c)(1),
(2) Date: Sep. 5, 2017

(87) PCT Pub. No.: WO2016/142199
PCT Pub. Date: Sep. 15, 2016

(65) Prior Publication Data
US 2018/0055810 A1    Mar. 1, 2018

(30) Foreign Application Priority Data
Mar. 6, 2015    (EP) .................................... 15158004

(51) Int. Cl.
*A61K 31/282*    (2006.01)
*C07F 15/00*    (2006.01)
*A61K 31/10*    (2006.01)
*G01R 33/46*    (2006.01)

(52) U.S. Cl.
CPC ............. *A61K 31/282* (2013.01); *A61K 31/10* (2013.01); *C07F 15/0093* (2013.01); *G01R 33/46* (2013.01)

(58) Field of Classification Search
None
See application file for complete search history.

(56) References Cited

U.S. PATENT DOCUMENTS

| | | | |
|---|---|---|---|
| 4,273,755 | A | 6/1981 | Rhoda et al. |
| 9,365,601 | B2 | 6/2016 | Jost et al. |

FOREIGN PATENT DOCUMENTS

| | | |
|---|---|---|
| EP | 2740737 A1 | 6/2014 |
| JP | S56054233 A | 5/1981 |
| JP | 2014114286 A | 6/2014 |

OTHER PUBLICATIONS

International Search Report for PCT/EP2016/054234 dated Apr. 20, 2016.
Written Opinion of the International Searching Authority for PCT/EP2016/054234 dated Apr. 20, 2016.
Alderden, R., et al., "The Discovery and Development of Cisplatin", Journal of Chemical Education, vol. 83, No. 1, (2006), pp. 728-734.
Office action for related Japanese Application No. 2017-546831 dated Dec. 16, 2019 (English translation).
Wilson, J.J., et al., "Synthetic Methods for the Preparation of Platinum Anticancer Complexes", Chemical Reviews, vol. 114, No. 8, (2014), pp. 4470-4495.

*Primary Examiner* — Po-Chih Chen
(74) *Attorney, Agent, or Firm* — Drinker Biddle & Reath LLP

(57) ABSTRACT

The present patent application relates to a novel organometallic compound, a process for the preparation thereof, and its use.

16 Claims, 4 Drawing Sheets

ORGANOMETALLIC COMPOUND

CROSS-REFERENCE TO RELATED APPLICATIONS

This application is a national stage application (under 35 U.S.C. § 371) of PCT/EP2016/053591, filed Feb. 19, 2016, which claims benefit of European Application No. 15160945.0, filed Mar. 26, 2015.

In chemotherapy for cancerous diseases, cytostatic agents that use complex compounds of the precious metal platinum as active ingredients (API) are used, such as cisplatin, carboplatin, or oxaliplatin, among others.

A possible intermediate stage, e.g., in the manufacturing process for carboplatin, is the cis-diammine-diaqua platinum complex cis-[$NH_3$)$_2$Pt($H_2O$)$_2$]$^{2+}$. Because this complex can occur as an impurity in an incomplete reaction in the carboplatin product, this complex is specified with an upper limit in the product.

An analytical standard is necessary to analyze the active ingredients during quality control using HPLC (high-performance liquid chromatography).

cis-diamminedinitratoplatinum cis-[($NH_3$)$_2$Pt($NO_3$)$_2$], CAS 41575-87-5) is the previously common precursor for the cis-diammine-diaqua platinum complex in carboplatin.

The common standard cis-[($NH_3$)$_2$Pt($NO_3$)$_2$] is a salt, which, when dissolved in water, disassociates to the doubly positively charged cis-diammine-diaqua platinum complex cis-[($NH_3$)$_2$Pt($H_2O$)$_2$]$^{2+}$ and two nitrate anions $NO_3$—.

The compound cis-[($NH_3$)$_2$Pt($NO_3$)$_2$] is a dry solid. It is known that dry compounds of ammonia and nitrate can tend towards spontaneous exothermic decomposition or even to explosion—especially when energy is supplied, such as by a shock or impact. This standard is therefore questionable as regards safety and should not be handled without extensive safety precautions.

EP-A-2740737 describes the dihydrate of 1,2-cyclohexandiaminplatinum(II)bis-(4-methylbenzolsulfonate) and a method for its manufacture.

Bartocci et al., Inorganica Chimica Acta 53, (1981), L157-L159, shows the compound cis-[Pt($NH_3$)$_2$($H_2O$)$_2$]$SO_4$, its manufacture, and polymers. In general, these polymers are described as Pt-blues and are always described as dimers or polymers of the cis-[Pt($NH_3$)$_2$($H_2O$)]$^{2+}$ complex.

These are described in Bartocci et al. using the following formula:

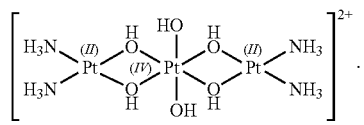

Appleton et al., Inorganica Chimica Acta 64, (1982), L229-L233, Appleton et al., Inorganic Chemistry Vol. 23, no. 22, (1984), 3514-3521, Flynn et al., J. Inorg. Nucl. Chem. 39, (1977), 437-439, and Lippert et al., Inorganic Chemistry Vol. 16, no. 6, (1977), 1525-1529, describe several diammine-diaqua complexes as well as their polymerization, wherein there are several undefined polymers, whose structure is, in part, not fully explained and which are described as "platinum blues."

It was therefore the aim to prepare a new compound, which yields the same cis-diammine-diaqua platinum complex cis-[$NH_3$)$_2$Pt($H_2O$)$_2$]$^{2+}$ in an aqueous solution as the then-common standards, that can be isolated as a solid and is stable over a longer time. In addition, this compound must be able to be reliably analyzed and easy to dissolve in water, and not be prone to decomposition reactions.

This aim was achieved by the compound cis-[($NH_3$)$_2$Pt($H_2O$)$_2$](O-Tos)$_2$, cis-(diammine-diaqua) platinum di-(p-toluenesulfonate) of the formula,

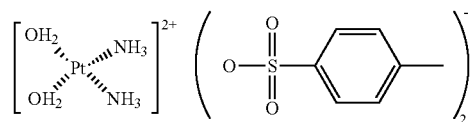

and polymers thereof. This compound can be obtained with a high purity and a low silver content of 3-70 ppm. The polymers are expected to have a structure similar to that described by Bartocci et al., Inorganica Chimica Acta 53 (1981), L157-L159 (see above). The stereochemistry of the cation can also be more clearly represented in this form:

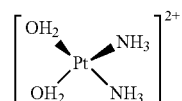

The product can be obtained by a method for manufacturing this compound with the following steps:
a) providing a specific amount of a cis-diamminedihalide Pt (II) complex in an aqueous solution or suspension;
b) conversion of this cis-diamminedihalide Pt (II) complex with the 1.8- to 2.2-fold molar amount (with respect to the cis-diamminedihalide Pt (II) complex) of silver-p-toluenesulfonate at a temperature of less than 100° C. while stirring;
c) optional addition of alkaline or alkaline earth halide to precipitate excess silver ions;
d) simple or multiple filtration for the separation of insoluble silver halides;
e) precipitation of the reaction product;
f) filtration of the reaction product in order to obtain a solid reaction product and the filtrate, as well as an optional washing of the reaction product.

SHORT DESCRIPTION OF THE INVENTION

1. The compound cis-[($NH_3$)$_2$Pt($H_2O$)$_2$](O-Tos)$_2$, cis-(diammine-diaqua)platinum di-(p-toluenesulfonate) of the formula,

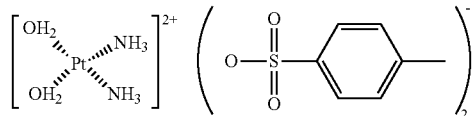

and polymers thereof,
2. Method for the preparation of the compound according to point 1, characterized by the following steps:
  a) providing a specific amount of a cis-diamminedihalide Pt (II) complex in an aqueous solution;
  b) conversion of this cis-diamminedihalide Pt (II) complex with the 1.8- to 2.2-fold molar amount (with respect to the cis-diamminedihalide Pt (II) complex) of silver-p-toluenesulfonate at a temperature of less than 100° C. while stirring;
c) optional addition of alkaline or alkaline earth halide to precipitate excess silver ions;
d) simple or multiple filtration for the separation of insoluble silver halides;
e) precipitation of the reaction product;
f) filtration of the reaction product in order to obtain a solid reaction product and the filtrate, and an optional washing of the reaction product.

3. Method according to point 2, wherein the precipitation in step e) is accomplished by distilling off water under reduced pressure at a temperature below 50° C. by addition of a precipitant or combinations thereof.

4. Method according to point 3, wherein about 75% to about 65% of the water is distilled off.

5. Method according to point 3, wherein the precipitant is an organic solvent, in particular, ethanol or acetone.

6. Method according to one or more of points 2 through 5, wherein step c) includes a precipitation step for the precipitation of excess alkaline earth ions.

7. Method according to one or more of points 2 through 6, wherein the silver-p-toluenesulfonate is used in the doubled molar amount vis-à-vis the cis-diamminedihalide Pt (II) complex.

8. Method according to one or more of points 2 through 7, wherein step a), providing the cis-diamminedihalide Pt (II) complex, is carried out by reaction of $K_2PtCl_4$ with potassium iodide and ammonia.

9. Method according to one or more of points 2 through 8, including the additional step g), in which the filtrate is cooled to a temperature between 0° C. and 10° C., and the precipitated reaction product is filtered off.

10. Method according to one or more of points 2 through 9, wherein step f) or g) is followed by an additional step for crystallizing the end product, in particular at least one step selected from the group consisting of recrystallization, a repetition of steps f) and g), and combinations thereof.

11. Method according to one or more of points 2 through 10, wherein, in step e), the pH value is adjusted to a pH value of 1.5 or less, advantageously, to 1 or lower—by the addition of an acid prior to precipitation.

12. Method according to point 11, wherein an organic or an inorganic acid is used.

13. Method according to one or more of points 11 through 12, wherein the inorganic acid is chosen from hydrochloric acid (HCl), sulfuric acid ($H_2SO_4$), or nitric acid ($HNO_3$).

14. Method according to one or more of points 11 through 12, wherein the organic acid is chosen from formic acid, acetic acid, p-toluenesulfonic acid, p-toluenesulfonic acid monohydrate, tartaric acid, citric acid, or cyclobutane-dicarboxylic acid.

15. Method according to one or more of points 2 through 14, wherein the filtered-off reaction product from steps f) or g) is dried in the absence of oxygen.

16. Method according to one or more of points 2 through 15, wherein the method is carried out in the absence of light, absence of oxygen, or combinations thereof.

17. Method according to one or more of points 2 through 16, wherein a cis-diamminediiode Pt (II) complex, cis-diamminedichloride Pt (II) complexes, or cis-diamminedibromide Pt (II) complexes, in particular, cis-diamminediiodide Pt (II) complexes, especially, platinum cis-diamminediiodide, are used as a cis-diamminedihalide Pt (II) complex.

18. Method for manufacturing a composition containing water, cis-(diammine-diaqua)platinum di-(p-toluenesulfonate) and optional further substances, wherein cis-(diammine-diaqua)platinum di-(p-toluenesulfonate) according to one or more of claims 2 through 17 is manufactured and dissolved in water or an aqueous solution.

19. Compound cis-(diammine-diaqua)platinum di-(p-toluenesulfonate) according to point 1 having a silver content of 3 to 70 ppm.

20. cis-(diammine-diaqua)platinum di-(p-toluenesulfonate) according to point 1, obtainable according to one or more of points 2 through 17.

21. Use of cis-(diammine-diaqua)platinum bis-(p-toluenesulfonate) according to point 1 or preparations thereof as an analytical standard.

22. Analysis kit containing cis-(diammine-diaqua)platinum di-(p-toluenesulfonate) according to point 1 or cis-(diammine-diaqua)platinum bis-(p-toluenesulfonate) obtainable according to one or more of points 2 to 17, or preparations thereof.

23. Use of the compound according to point 1 as a precursor for the synthesis of cytostatic active platinum complexes.

24. Use of the compound according to point 1 as an active substance in cytostatic agents.

DETAILED DESCRIPTION OF THE INVENTION cis-diamminediiode Pt (II) complexes, cis-diamminedichloride Pt (II) complexes, or cis-diamminedibromide Pt (II) complexes, in particular, cis-diamminediiodide Pt (II) complexes, can be advantageously used as a cis-diamminedihalide Pt (II) complex. Platinum cis-diamminediiodide, which can be obtained by reaction of $K_2PtCl_4$ with potassium iodide and ammonia (Inorganic Syntheses (1989), 25, 98-100), is particularly suitable. The product is obtained by reaction of the cis-diamminedihalide Pt (II) complex, in particular, cis-diamminediiode Pt (II) complex, with the 1.8- to 2.2-fold molar amount (with respect to the cis-diamminedihalide Pt (II) complex or cis-diamminediiode Pt (II) complex), or the 1.9- to 2.1-fold molar amount, in particular, the doubled molar amount of silver-p-toluenesulfonate in an aqueous solution.

The reaction can be carried out so that an aqueous solution or suspension of the cis-diamminedihalide Pt (II) complex—in particular, of the cis-diamminediiode Pt (II) complex—specifically, platinum-cis-diamminediiodide—is produced and combined with solid silver-p-toluenesulfonate.

Alternately, the silver-p-toluenesulfonate can also be produced in situ in the reaction mixture, for example, by reaction of silver oxide and tolulenesulfonic acid. This can be done inside a reaction vessel, and the cis-diamminedihalide Pt (II) complex is then added as, for example, a solid, solution, or suspension. The in situ production of silver-p-toluenesulfonate can, however, also take place in a second reaction vessel and then be added to the produced cis-diamminedihalide Pt (II) complex.

In the case of a suspension, the undissolved cis-diamminedihalide Pt (II) complex or cis-diamminediiode Pt (II) complex gradually dissolves in the course of the reaction. The concentration of cis-diamminedihalide Pt (II) complex or cis-diamminediiode Pt (II) complex or its relationship to the solvent water is generally uncritical and is based upon the existing production facilities. A not unduly large amount of solvent should be selected for a rapid reaction; because of the limited water solubility of this reagent, however, not too small an amount. Weight ratios of cis-diamminedihalide Pt (II) complex or cis-diamminediiode Pt (II) complex to water in a range from 1:100 to 100:1, or from 5:100 to 20:100, or 8:100 to 10:100, have proven effective.

The reaction is carried out at below 100° C. while stirring. Temperatures in a range from 40° C. to 90° C., or from 50° C. to 80° C., or from 60° C. to 75° C. have proven effective. The reaction time is usually about 2 to 24 hours—in particular, about 4 to 16 hours or about 6 to 12 hours.

If silver-p-toluenesulfonate is used in an amount of less than double molar quantity (with respect to the cis-diamminedihalide Pt (II) complex or cis-diamminediiode Pt (II) complex), either a sufficiently high amount of water must be used in order to maintain unreacted cis-diamminedihalide Pt (II) complex in aqueous solution, or, alternately, the reaction product must be washed for a sufficiently long time or recrystallized. This becomes less critical as the amount of silver-p-toluenesulfonate increases; starting at a two-fold molar amount of silver-p-toluenesulfonate, an essentially quantitative reaction generally occurs, so that the amount of unreacted cis-diamminedihalide Pt (II) complex in the reaction procedure no longer needs to be taken into account.

If the silver-p-toluenesulfonate in amounts of more than the doubled molar amount (with respect to the cis-diamminedihalide Pt (II) complex) is used, the addition of alkaline or alkaline earth halides is recommended in order to precipitate excess silver in the form of silver halide.

The alkaline or alkaline earth halide can be chosen from the group consisting of chlorides, bromides, iodides or fluorides of sodium, potassium, lithium, rubidium, cesium, beryllium, magnesium, calcium, strontium, barium, and mixtures thereof. It is recommended that well-water-soluble compounds be selected because, in this manner, as much alkaline or alkaline earth halide as possible can be dissolved into the least possible water volume. These are, for example, chlorides or bromides of sodium or potassium—particularly, sodium chloride or potassium chloride.

In the event that alkaline earth halides are used, excess alkaline earth metal ions can also be precipitated again by adding the appropriate precipitant, e.g., by adding carbonic acid in order to precipitate excess calcium chloride as calcium carbonate or by adding sulfuric acid to precipitate excess barium or strontium. However, the alkali metal halides—in particular, chlorides or bromides of sodium or potassium—especially, sodium chloride or potassium chloride—are generally preferred.

The reaction mixture is then filtered until a clear solution is obtained. Repeated filtration via a glass frit, specifically, a G4 glass frit, as necessary, has proven effective for this.

The reaction product is then precipitated from this clear solution. In one embodiment of the invention, this can be achieved by the addition of precipitants. Particularly suitable for this are polar organic solvents, in which the reaction product is insoluble or poorly soluble. These must not react with the reaction product, e.g., by undergoing a ligand exchange, and must also be sufficiently water soluble. Acetone and ethanol, for example, are very suitable. Alternately, water can be removed from the reaction mixture, in particular, distilled off, until the reduction product precipitates. In particular, this is done under reduced pressure at a temperature of less than 50° C., and can be conveniently carried out with standard rotary evaporators. Good results can be achieved by removing about 75% to about 65% of the water. The reaction product can then be filtered off and optionally washed, wherein water, cold water, and organic solvents, such as ethanol or acetone, are suitable for use as a washing medium.

If, before precipitating the reaction product, the pH value is adjusted to a pH value of 1.5 or less, advantageously, of 1 or lower, by the addition of an acid prior to precipitation, monomeric reaction product cis-(diammine-diaqua)platinum di-(p-toluenesulfonate) is obtained. If the adjustment of the pH value is omitted, one also obtains polymeric cis-(diammine-diaqua)platinum di-(p-toluenesulfonate). The acids used to adjust the pH value must not undergo a ligand exchange with the platinum atom of the reaction product, because then the desired product is not obtained. Organic or inorganic acids can be used for this, such as hydrochloric acid (HCl), sulfuric acid ($H_2SO_4$), nitric acid ($HNO_3$), formic acid, acetic acid, p-toluenesulfonic acid, p-toluenesulfonic acid monohydrate, tartaric acid, citric acid, cyclobutane dicarbolic acid, or combinations thereof.

To optimize the yield, the filtrate may be cooled to a temperature between 0° C. and 10° C., wherein additional reaction product precipitates and can be filtered off. Filtration via a G4 glass frit has also proven effective here.

Additional steps can be performed here, such as crystallization of the end product. To this end, water can be removed from the filtrate and filtered, and/or cooled and filtered again if necessary.

A recrystallization from water is also possible, wherein, after the renewed dissolution, the reaction product must be precipitated again, either by concentrating the solution, cooling the solution, or a combination thereof, wherein precipitating reaction product is again filtered off and, as described above, washed if applicable.

The cis-(diammine-diaqua-platinum) di-(p-toluenesulfonate) thus obtained can be dried after filtration. This is advantageously performed using inert gas under reduced pressure.

It is especially advantageous if oxygen is excluded during the course of the reaction, as far as possible, for which, for example, the equipment to be used for the production is evacuated and refilled with inert gas, and the solvent and precursors are degassed and stored in inert gas. Nitrogen and argon, in particular, are suitable inert gases. Exclusion of light is also advisable.

The compound cis-(diammine-diaqua-platinum) bis-(p-toluenesulfonate), which can be obtained according to the method described above, is appropriate for use as an analytical standard in the manufacture or analysis and quality control of platinum-containing cytostatic agents, such as cisplatin, carboplatin, or oxaliplatin. The present patent application thus also relates to the use of cis-(diammine-diaqua-platinum) bis-(p-toluenesulfonate) and preparations thereof as an analytical standard.

The analysis is generally performed using high-performance liquid chromatography (HPLC). cis-(diammine-diaqua-platinum) bis-(p-toluenesulfonate) should therefore be dissolved in a solvent before use, in particular water —. The present patent application thus also relates to a method for manufacturing a composition containing water, cis-(diammine-diaqua-platinum) di-(p-toluenesulfonate) and optional further substances, wherein cis-(diammine-diaqua-platinum) di-(p-toluenesulfonate) is dissolved in water or an aqueous solution.

Auxiliary materials, stabilizers, or known by-products or reactants can be used as additional substances and are used in the production of platinum-containing cytostatic agents such as carboplatin or oxaliplatin, e.g., cyclobutane dicarbolic acid, cyclohexane diamine, or also ethanedioic acid.

The compound cis-(diammine-diaqua-platinum) di-(p-toluenesulfonate), as well as preparations thereof, can also be produced, distributed, and used in analysis kits for analysis or determination of platinum-containing cytostatic agents. The present patent application thus also relates to an analysis kit for analyzing platinum-containing cytostatic agents containing cis-(diammine-diaqua-platinum) di-(p-toluenesulfonate), as well as preparations containing this compound.

cis-diammine-diaqua platinum complex cis-$[(NH_3)_2Pt(H_2O)_2]^{2+}$ occurs as an intermediate product in the manufacture of many platinum-containing cytostatic active platinum complexes (such as carboplatin or cis-platinum), wherein cis-(diammine-diaqua)platinum di-(p-toluenesulfonate), (cis-$[(NH_3)_2Pt(H_2O)_2](O\text{-}Tos)_2$) and its polymers can serve as sources for the cis-diammine-diaqua platinum complex cis-$[NH_3)_2Pt(H_2O)_2]^{2+}$. The present patent application also relates to the use of (diammine-diaqua)platinum di-(p-toluenesulfonate), (cis-$[(NH_3)_2Pt(H_2O)_2](O\text{-}Tos)_2$) and its polymers as precursors for the synthesis of cytostatically active platinum complexes.

An additional possibility for use of the compound cis-(diammine-diaqua)platinum di-(p-toluenesulfonate), (cis-$[(NH_3)_2Pt(H_2O)_2](O\text{-}Tos)_2$) and its polymers is the use as an active ingredient, i.e., as an active pharmaceutical ingredient (API) and thus as a component of medicinal products (pharmaceuticals) having a cytostatic effect—so-called cytostatic agents. The present patent application therefore also relates to the use of cis-(diammine-diaqua)platinum di-(p-toluenesulfonate), (cis-$[(NH_3)_2Pt(H_2O)_2](O\text{-}Tos)_2$) and its polymers as active substances in cytostatic agents, as well as medical products containing cis-(diammine-diaqua) platinum di-(p-toluenesulfonate), (cis-$[(NH_3)_2Pt(H_2O)_2](O\text{-}Tos)_2$) and its polymers as an active pharmaceutical ingredient (API).

EXAMPLES

Example 1

A 250 ml three-neck flask was flushed for 15 minutes with a stream of argon at 0.01 m$^3$/h (10 L/h) and thereby rendered inert. The stream was then reduced to 0.005 m$^3$/h (5 L/h), and 7.5 g cis-Pt(NH$_3$)$_2$I$_2$ presented and added to 100 ml degassed, distilled water and stirred. While being stirred, 8.67 g silver tosylate was added via a powder funnel in an argon counter-current, and the weighing tray and powder funnel were rinsed with 50 ml of degassed, distilled water. The reaction mixture was heated to 70° C. and stirred for 6 hours at 70° C. The heat supply was then stopped, and the mixture was allowed to cool to room temperature for approximately 16 hours while being stirred. Filtration took place in an argon atmosphere via a G4 reverse frit and the filter cake was washed twice using 5 ml of degassed, distilled water.

The pH value was adjusted to 1 by the addition of approximately 3 ml p-tolulenesulfonic acid monohydrate, and 115 ml of water was distilled off at a temperature of 28° C. and a pressure of approximately 3 kPa (30 mbar), wherein a crystalline deposit was precipitated out. This was filtered off via a G4 reverse frit in an argon atmosphere and dried in a stream of argon. The filtrate was cooled for approximately 16 hours in a refrigerator to 7° C., wherein a crystalline deposit was again precipitated out. This was also filtered off and dried.

Elemental Analysis: Pt, 31.77%, C, 27.3%, H, 4.4%, N, 5%, S, 11.20%, Ag, 10 ppm, I, 25 ppm.

(Theory: Pt, 32.11%, C, 27.68%, H, 3.98%, N, 4.61%, S, 10.56%, Ag, 0 ppm, I, 0 ppm)

NMR ($^{195}$Pt): δ =−1573.47 (s)

Figure 1:
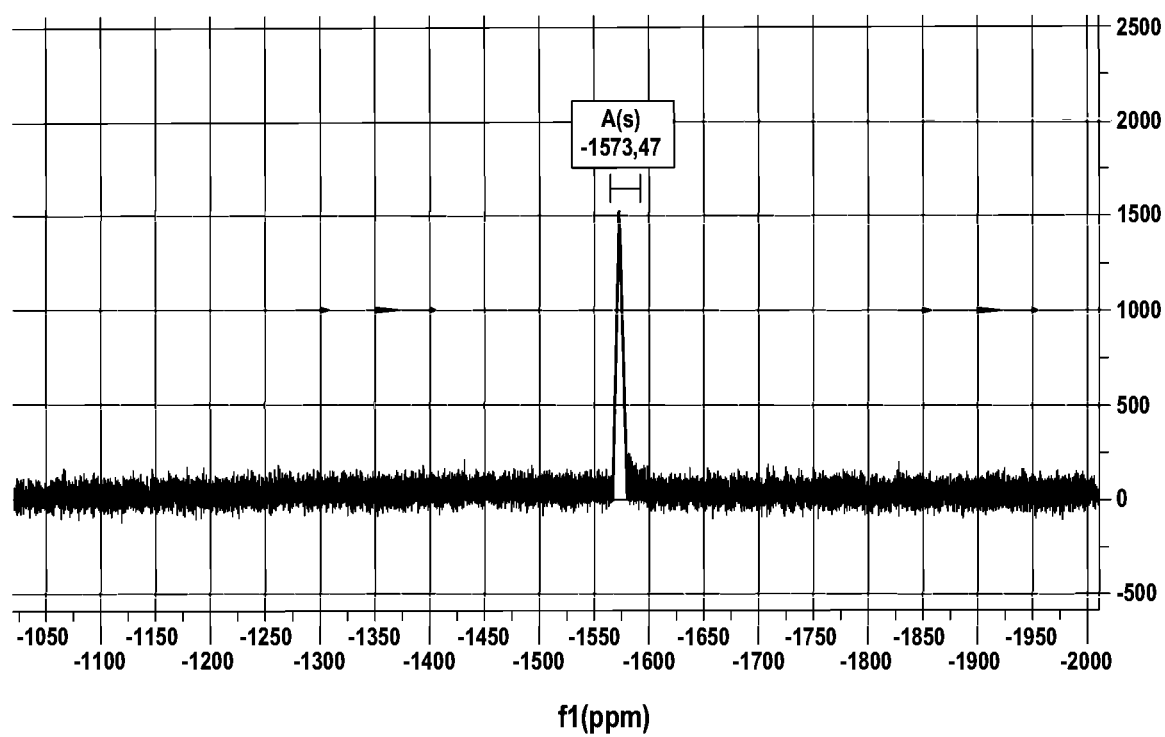
FIG. 1 is a figurative representation of the $^{195}$Pt-NMR spectrum.

FIG. 1 is a figurative representation of the $^{195}$Pt-NMR spectrum.

Figure 2:
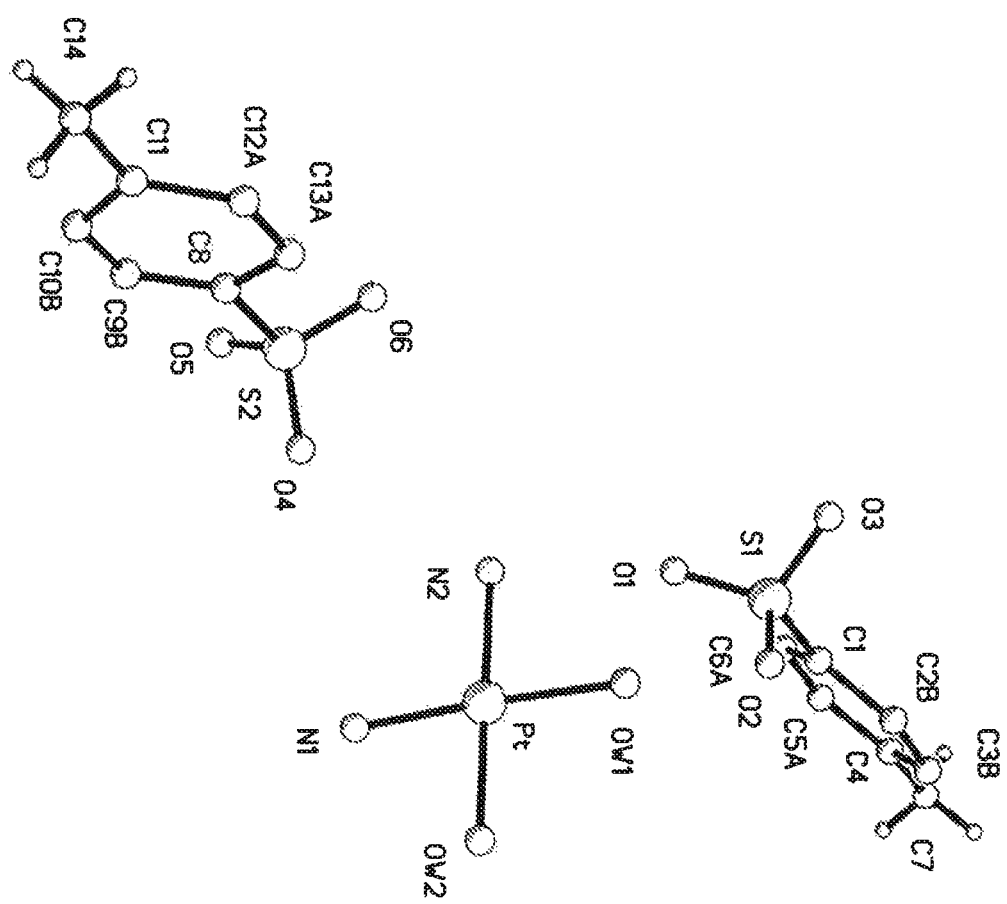
FIG. 2 shows the structure of the compound, determined by single-crystal x-ray analysis.

FIG. 2 shows the structure of the compound, determined by single-crystal x-ray analysis.

Structural Data from the Single-crystal X-ray Analysis:

| | |
|---|---|
| Empirical formula | C$_{14}$H$_{24}$N$_2$O$_8$PtS$_2$ |
| Measuring temperature | 293 K |
| Wavelength | 71.073 pm (MoKα, graphite monochromator) |
| Crystal system | monoclinic |
| Space group | P2$_1$/n (no. 14) |
| Lattice constants | a = 616.50 (10) pm     α = 90° |
| | b = 1380.3(2) pm     β = 92.758(9)° |
| | c = 2386.0(3) pm     γ = 90° |
| Elementary cell volume | 2028.0(5) · 10$^6$ pm$^3$, Z = 4 |
| Θ field | 2.26-25.0° |
| Index area | h −1/7 |
| | k −1/16 |
| | l −28/28 |

The yield is approximately 62% (relative to the platinum used).

Example 2

In a 250 ml three-necked flask rendered inert using argon, 11.1 g cis-Pt(NH$_3$)$_2$I$_2$ was provided and 120 ml degassed, distilled water was added and stirred. 12.85 g silver tosylate was added while the mixture was stirred, and the weighing tray and powder funnel were washed with 20 ml of distilled water. The reaction mixture was heated to 70° C. and stirred for 6 hours at 70° C. The heat supply was then stopped, and the mixture was allowed to cool to room temperature for approximately 16 hours while being stirred. Filtration took place in an argon atmosphere via a G4 reverse frit, and the filter cake was washed twice using 5 ml of degassed, distilled water.

Water was distilled from the resulting solution at a temperature of 31° C. and a pressure of 1.5 kPa (15 mbar) until dry, wherein a crystalline deposit was precipitated.

This was again dried in the argon flow under reduced pressure.

The product has a gray-blue color, which indicates a polymeric species according to the literature (among others, Bartocci et al.; see above).

Yield: 95.1%

Elemental Analysis: Pt, 31.96%, C, 27.3%, H, 4.3%, N, 4.7%, S, 11.85%, Ag, 8 ppm, I, 15 ppm) (Theory for the monomer: Pt, 32.11%, C, 27.68%, H, 3.98%, N, 4.61%, S, 10.56%, Ag, 0 ppm, I 0 ppm)

Figure 3:
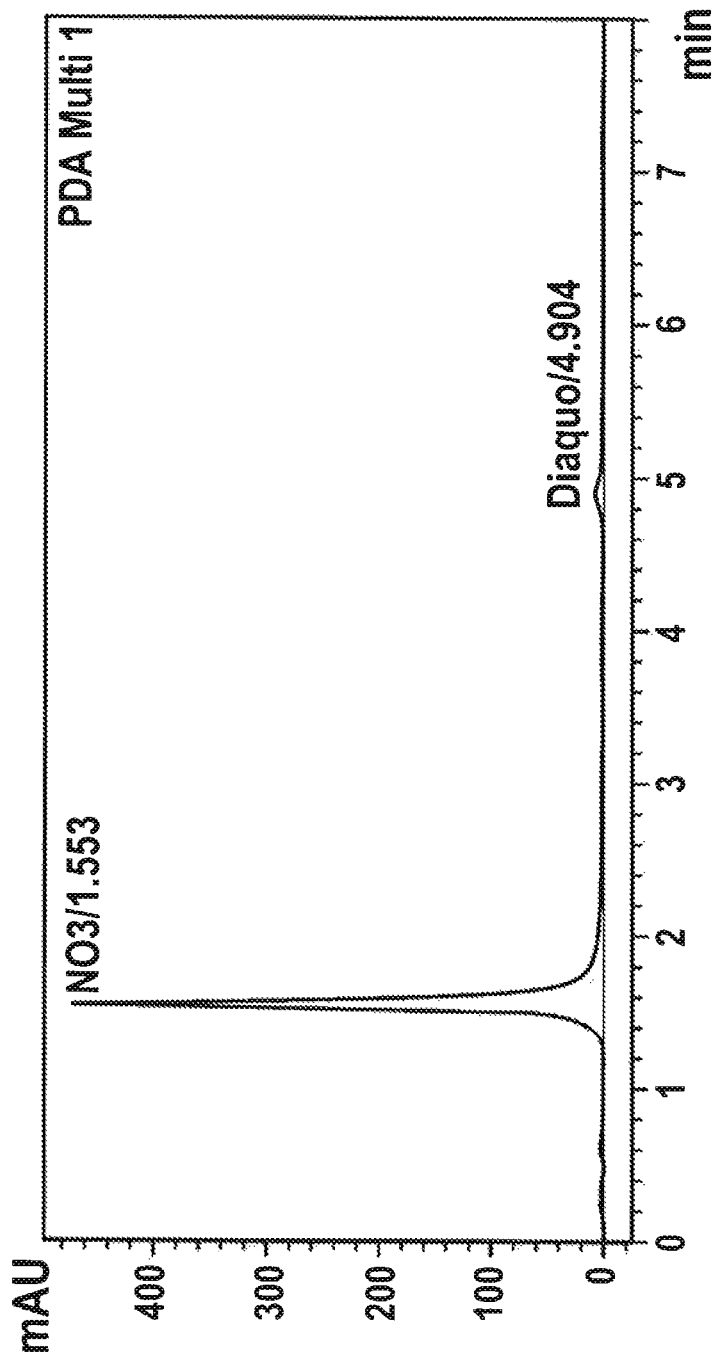
FIG. 3 shows an HPLC chromatogram of cis-diamminedinitrate platinum cis-$[(NH_3)_2Pt(NO_3)_2]$, CAS 41575-87-5).

Use of cis-(diammine-diaqua)platinum di-(p-toluenesulfonate) as an analytical standard FIG. 3 shows an HPLC chromatogram of cis-diamminedinitrate platinum cis-[NH$_3$)$_2$Pt(NO$_3$)$_2$], CAS 41575-87-5). Easily recognizable is the strong peak at a retention time of 1.553 minutes that results from nitration and the weaker peak at a retention time of 4.904 minutes, which indicates the presence of the cis-diammine-Pt-diaquo complex.

Figure 4:
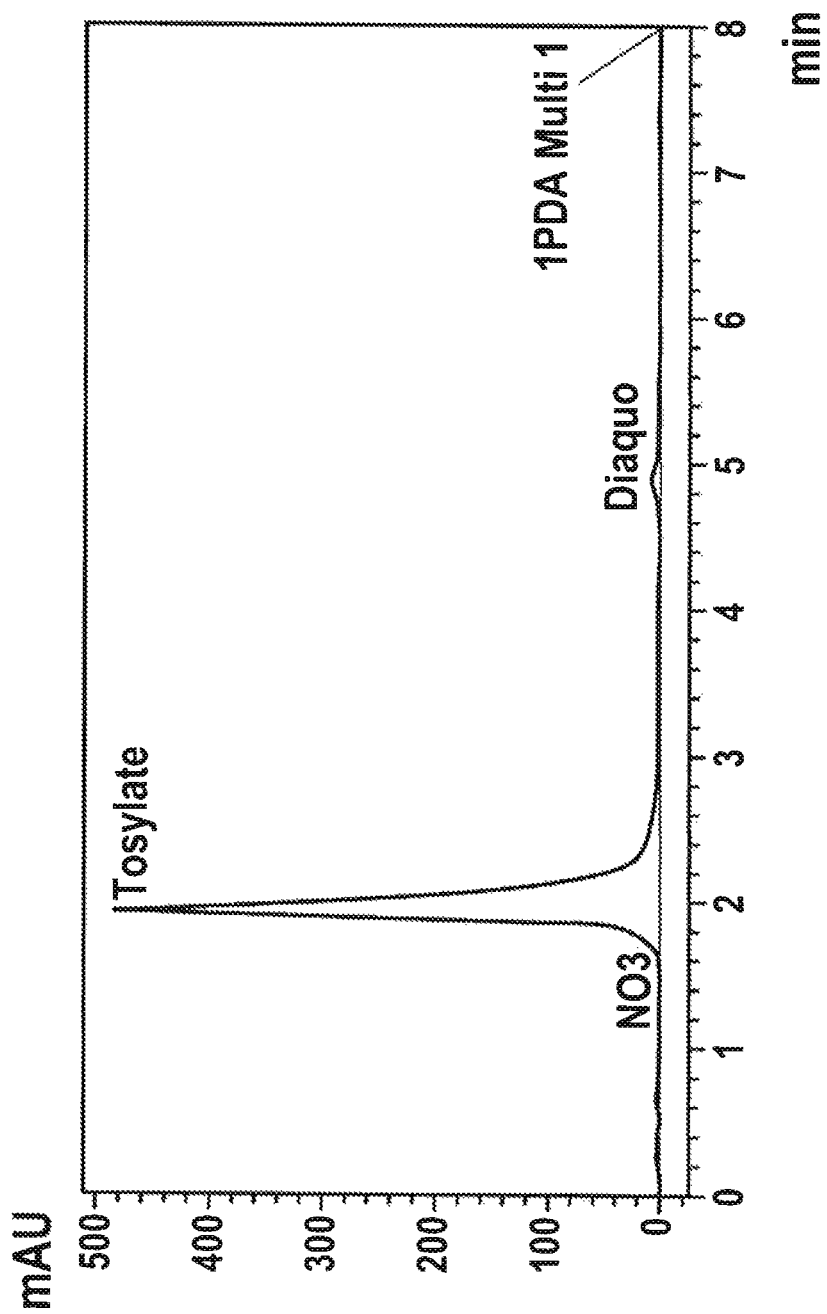
FIG. 4 shows an HPLC chromatogram of cis-(diammine-diaqua)platinum di-(p-toluenesulfonate), cis-$[(NH_3)_2Pt(H_2O)_2](O\text{-}Tos)_2$.

FIG. 4 shows an HPLC chromatogram of cis-(diamminediaqua)platinum di-(p-toluenesulfonate), cis-[(NH$_3$)$_2$Pt(H$_2$O)$_2$](O-Tos)$_2$. The nitrate peak at a retention time of 1.553 minutes is only poorly recognizable; the weaker peak of the cis-diammine-Pt-diaquo complex also falls at a retention time of 4.903 minutes. A stronger peak at a retention time of 1.941 minutes is caused by the tosylate ion.

It can thus be stated that the compound according to the invention is suitable as an analytical standard, because the desired cis-diammine-Pt-diaquo complex is provided.

The invention claimed is:

1. A compound, which is cis-(diammine-diaqua)platinum di-(p-toluenesulfonate) of the formula,

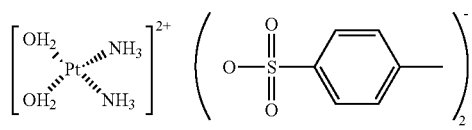

and polymers thereof.

2. A analytical standard comprising the cis-(diamminediaqua)platinum bis-(p-toluenesulfonate) according to claim 1.

3. An analysis kit containing cis-(diammine-diaqua)platinum di-(p-toluenesulfonate) according to claim 1.

4. A precursor for synthesis of cytostatic active platinum complexes comprising the compound according to claim 1.

5. A cytostatic agent comprising the compound according to claim 1 as an substance.

6. A method for the preparation of the compound according to claim 1, comprising:
   a) providing a specific amount of a cis-diamminedihalide Pt (II) complex in an aqueous solution;
   b) conversion of this cis-diamminedihalide Pt (II) complex with the 1.8- to 2.2-fold molar amount, with respect to the cis-diamminedihalide Pt (II) complex of silver-p-toluenesulfonate at a temperature of less than 100° C. while stirring to form a reaction product having a pH value;
   c) optional addition of alkali metal halide or alkaline earth metal halide to precipitate excess silver ions;
   d) simple or multiple filtration for separation of insoluble silver halides;
   e) precipitation of the reaction product;
   f) filtration of the reaction product in order to obtain a solid reaction product and the filtrate, and an optional washing of the reaction product.

7. The method according to claim 6, wherein the precipitation in step e) is accomplished by the distilling off water under reduced pressure at a temperature below 50° C., by addition of a precipitator or combinations thereof, or by distilling off water under reduced pressure at a temperature below 50°C. and addition of precipitant.

8. The method according to claim 7, wherein about 75% to about 65% of the water is distilled off.

9. The method according to claim 7, wherein the precipitant is an organic solvent.

10. The method according to claim 6, wherein step c) includes a precipitation step of excess alkaline earth metal ions.

11. The method according to claim 6, wherein the silver-p-toluenesulfonate is used in the doubled molar amount vis-à-vis cis-diamminedihalide Pt (II) complex.

12. The method according to claim 6, including the additional step g), in which the filtrate is cooled to a temperature between 0° C. and 10° C., wherein additional reaction product precipitates, and the additional precipitated reaction product is filtered off.

13. The method according to claim 6, wherein, in step e), the pH value is adjusted to 1.5 or less, by addition of an acid prior to the precipitation.

14. The method according to claim 6, wherein the method is carried out in the absence of light, absence of oxygen, or combinations thereof.

15. A method for manufacturing a composition containing water, cis-(diammine-diaqua)platinum di-(p-toluenesulfonate) according to claim 1, and optional further substances, wherein cis-(diammine-diaqua)platinum di-(p-toluenesulfonate) is dissolved in water or an aqueous solution.

16. A compound of cis-(diammine-diaqua)platinum di-(p-toluenesulfonate) obtained by the method according to claim 6.

* * * * *